US00PP12931P2

(12) United States Plant Patent
Cupitt

(10) Patent No.: US PP12,931 P2
(45) Date of Patent: Sep. 10, 2002

(54) PULMONARIA PLANT NAMED 'OCUPOL'

(75) Inventor: Elisabeth Susan Cupitt, Halifax (GB)

(73) Assignee: Blooms of Bressingham Ltd., Bressingham (GB)

( * ) Notice: Subject to any disclaimer, the term of this patent is extended or adjusted under 35 U.S.C. 154(b) by 0 days.

(21) Appl. No.: 09/566,447

(22) Filed: May 8, 2000

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database, 2001/03, GTI Jouve Retrieval Software, citation for 'Ocupol'.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Pulmonaria plant named 'Ocupol', characterized by its attractive and dense silvery leaf spotting; freely flowering habit; and attractive and large light lavender flowers that open fully.

1 Drawing Sheet

BACKGROUND OF THE INVENTION

The present Invention relates to a new and distinct cultivar of Pulmonaria plant, botanically known as *Pulmonaria officinalis*, marketed under the trade name Opal, and hereinafter referred to by the cultivar name Ocupol.

The new Pulmonaria is a seedling from random open pollinations of various unidentified selections of *Pulmonaria officinalis*. The new Pulmonaria was discovered and selected by the Inventor in 1986 as a flowering plant in a controlled environment in Luddenden, Halifax, West Yorkshire, England. The new Pulmonaria was selected on the basis of large light lavender flowers and attractive silver leaf spotting.

Asexual reproduction of the new cultivar by cuttings and divisions taken at Bressingham, Diss, Norfolk, England, has shown that the unique features of this new Pulmonaria are stable and reproduced true to type in successive generations.

SUMMARY OF THE INVENTION

Plants of the cultivar Ocupol have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Ocupol'. These characteristics in combination distinguish 'Ocupol' as a new and distinct cultivar:

1. Attractive and dense silvery leaf spotting.
2. Freely flowering.
3. Attractive and large light lavender flowers that open fully.

Compared to unidentified selections of the *Pulmonaria officinalis* and the *Pulmonaria officinalis* cultivar 'Roy Davidson', not patented, plants of the new Pulmonaria have more silver leaf spotting, have larger flowers that open more fully, and lighter lavender flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ from the color values cited in the detailed botanical description which more accurately describe the actual colors of the new Pulmonaria.

The photograph at the top of the sheet comprises a side perspective view of a typical plant of 'Ocupol' grown in the landscape.

The photograph at the bottom of the sheet is a close-up view of typical flowers of 'Ocupol'.

DETAILED BOTANICAL DESCRIPTION

In the following description, color references are made to The Royal Horticultural Society Colour Chart except where general terms of ordinary dictionary significance are used. Plants were grown in Bressingham, Diss, Norfolk, England under field conditions which closely approximate commercial production conditions. Day temperatures ranged from 5 to 28° C. and night temperatures ranged from −8 to 15° C. Plants were observed when they were one year old.

Botanical classification: *Pulmonaria officinalis* cultivar Ocupol.

Parentage: Open-pollination of various unidentified selections of *Pulmonaria officinalis*, not patented.

Propagation:

*Type.*—By cuttings, divisions or by tissue culture.

*Time to initiate roots.*—Summer: About 10 days at 20° C. Winter: About 15 days at 10° C.

*Time to produce a rooted cutting or liner.*—Summer: About 15 days at 20° C. Winter: About 20 days at 10° C.

*Rooting habit.*—Fibrous and fleshy.

Plant description:

*Rate of growth.*—During one growing season in England, plants of the new Pulmonaria will grow to about 25 cm in height.

*Form.*—Low spreading; clumping; dense and bushy perennial.

*Usage.*—Appropriate for five-liter containers.

*Plant height, soil level to top of plant plane.*—About 25 cm.

*Plant width.*—About 45 cm.

*Internode length.*—About 4 cm.

*Stem texture.*—Pubescent.

*Stem color.*—147A.

*Foliage description.*—Leaves simple, generally symmetrical and long persisting. Length, mature leaves: About 30 cm. Width, mature leaves: About 9 cm. Shape: Ovate. Apex: Abruptly acute. Base: Attenuate. Margin: Entire. Texture: Rough; very pubescent. Color: Young foliage, upper surface: 147A; silver spots, 198D. Young foliage, lower surface: 147C. Mature foliage, upper surface: 147B; silver spot, 198D. Mature foliage, lower surface: 147C. Petiole: Length: About 8 cm. Diameter: About 4 mm. Color: Edge, 147A; center, 147C.

Flower description:

*Flower type and habit.*—Single funnel-shaped flowers arranged on compound cymes. Freely flowering. Flowers last about 20 days on the plant. Flowers persistent. Not fragrant.

*Natural flowering season.*—Continuously flowering from March to May in the northern hemisphere.

*Quantity.*—About 180 to 300 flowers and flower buds per plant.

*Flower diameter.*—About 1 cm.

*Flower depth* (*height*).—About 1 cm.

*Flower buds* (*just showing color*).—Length: About 8 mm. Diameter: About 4 mm. Shape: Ovoid. Color: 147B.

*Petals.*—Arrangement/appearance: Single whorl of five petals, funnel-shaped flowers. Length: About 8 mm. Width: About 5 mm. Shape: Lobed. Apex: Rounded. Margin: Entire. Texture: Smooth, soft. Color: Upper and lower surfaces, when opening: Initially 70D, changing to 97D as flowers develop. Upper surface, opened flower: 97C; fading to 97D with subsequent development. Lower surface, opened flower: 97C.

*Calyx.*—Shape: Funnel-shaped; sepals, five. Length: About 5 to 10 mm. Diameter: About 5 mm. Color, upper and lower surfaces: 147B.

*Peduncle.*—Strength: Stiff. Angle: Mostly erect. Length: About 15 cm. Color: 147B.

*Reproductive organs.*—Stamens: Quantity: Five. Anther length: About 2 mm. Anther shape: Cylindrical. Anther color: 202B. Pollen amount: Scarce. Pollen color: 157D. Pistils: Pistil quantity per flower: One. Pistil length: About 1 cm. Stigma shape: Pin-shaped. Stigma color: 145D. Style length: About 1 cm. Style color: 145D. Ovary color: 147A. Seed: Seed development has been observed; seed, small and black in color.

Disease resistance: Under commercial production conditions, plants of the new Pulmonaria have not been noted to be resistant to pathogens common to Pulmonaria.

It is claimed:

1. A new and distinct cultivar of Pulmonaria plant named 'Ocupol', as illustrated and described.

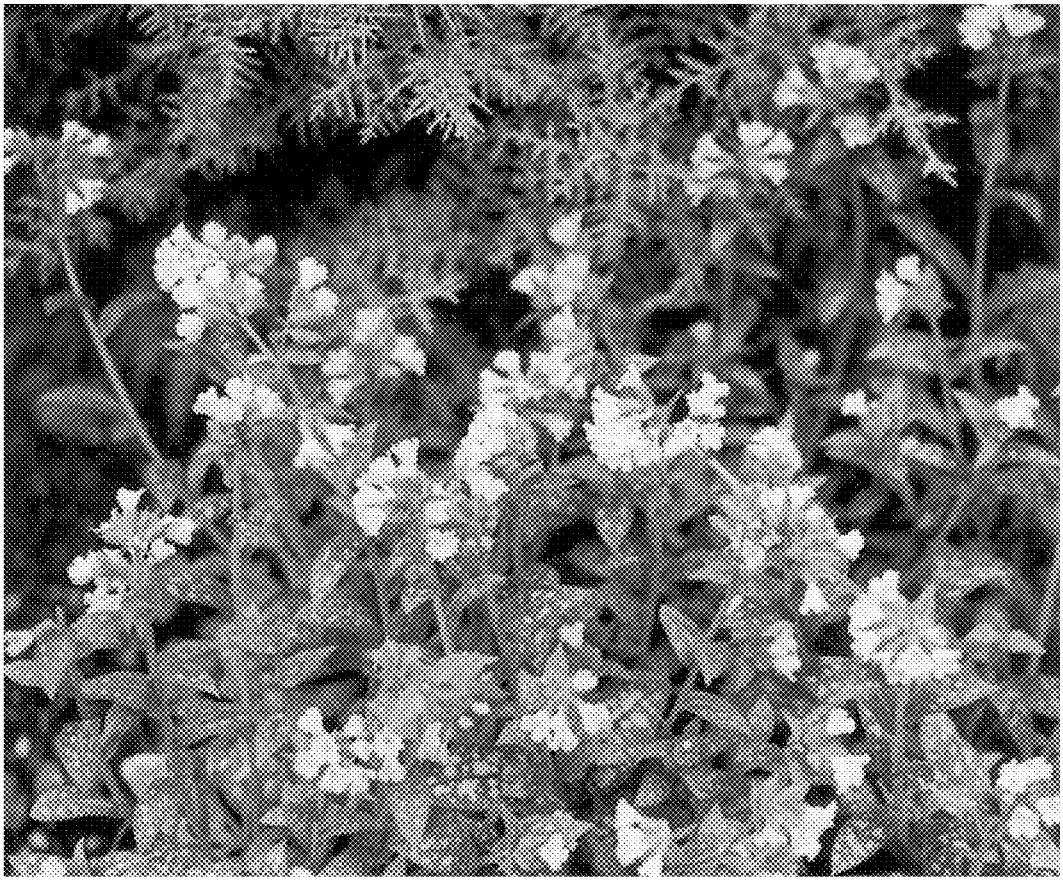
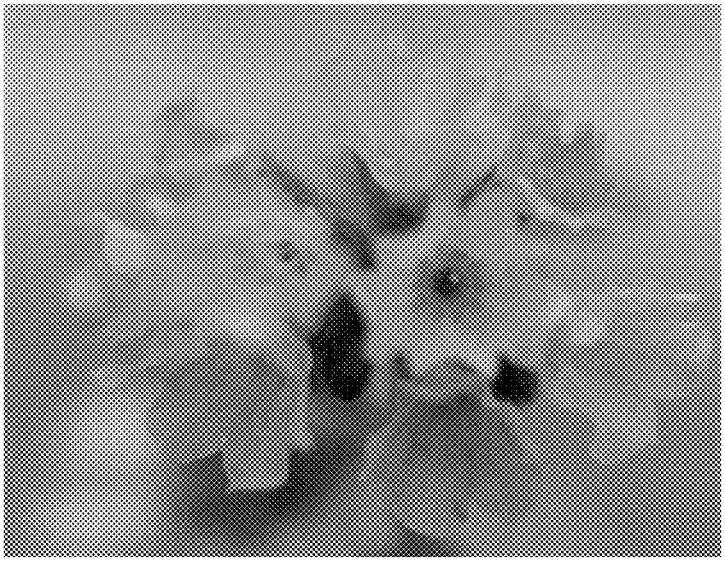

* * * * *